United States Patent
Illig et al.

Patent Number: 5,476,644
Date of Patent: Dec. 19, 1995

[54] CYCLIC TRIAMINE CHELATING AGENTS

[75] Inventors: Carl R. Illig, Phoenixville; Thomas J. Caulfield, Audubon; John L. Toner, Downingtown; Peng Guo, East Pikeland Township, Chester County; David L. Ladd, Wayne, all of Pa.

[73] Assignee: Sterling Winthrop Inc., New York, N.Y.

[21] Appl. No.: 227,161

[22] Filed: Apr. 13, 1994

[51] Int. Cl.[6] .................... A61K 43/00; A61K 49/00; A61K 31/28
[52] U.S. Cl. .................... 424/1.11; 424/9.34; 424/617; 424/630; 424/639; 424/646; 424/9.341; 424/9.35; 424/9.361; 424/9.364; 424/9.365; 514/492; 514/499; 514/501; 514/502; 514/505; 514/579; 534/10; 534/16; 556/44; 556/50; 556/61; 556/116; 556/148; 556/1; 560/125; 562/507; 564/152; 564/153; 564/191; 544/259; 546/1; 546/2; 546/104; 546/134; 546/255; 548/240; 548/446; 548/469; 549/211; 549/212; 549/388; 549/398
[58] Field of Search .................... 556/44, 50, 61, 556/116, 148, 1; 514/492, 499, 501, 502, 505, 579; 534/10, 16; 424/1.11, 9, 617, 630, 639, 646; 560/125; 562/507, 152, 153, 191; 544/259; 546/1, 2, 104, 134, 255; 548/240, 446, 469; 549/3, 29, 211, 212, 388, 398

[56] References Cited

U.S. PATENT DOCUMENTS

| | | | |
|---|---|---|---|
| 4,647,447 | 3/1987 | Gries et al. | 424/9 |
| 5,021,571 | 6/1991 | Mease et al. | 544/166 |
| 5,089,663 | 2/1992 | Mease et al. | 562/507 |
| 5,124,471 | 6/1992 | Gansow et al. | 558/17 |
| 5,344,729 | 8/1994 | Mease et al. | 548/546 |

FOREIGN PATENT DOCUMENTS

| | | |
|---|---|---|
| 0299795 | 1/1989 | European Pat. Off. |
| 86/06605 | 11/1986 | WIPO |
| 91/10669 | 7/1991 | WIPO |
| 91/10645 | 7/1991 | WIPO |
| 93/02045 | 2/1993 | WIPO |

*Primary Examiner*—Porfirio Nazario-Gonzalez
*Attorney, Agent, or Firm*—Fish & Richardson

[57] ABSTRACT

The present invention provides compounds of the formula

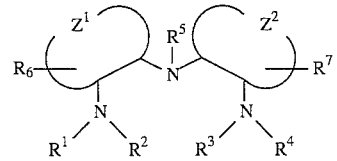

chelated with a paramagnetic metal ion wherein $Z^1$ and $Z^2$ each represent the atoms necessary to complete a monocyclic or polycyclic carbocyclic or heterocyclic ring system, said $Z^1$ and $Z^2$ independently optionally substituted with $R^6$ and $R^7$, respectively;

$R^1$, $R^2$, $R^3$ and $R^4$ are independently carboxyalkyl ($C_1$–$C_2$), —$(CH_2)_n$—C(=O)—NH—$R^8$, or —$(CH_2)_n$—C(=O)—O—$R^8$ $R^5$ is carboxyalkyl ($C_1$–$C_2$);

$R^6$ and $R^7$ are independently hydrogen, benzyl, or benzyloxy, said benzyl or benzyloxy optionally substituted with one, two or three substituents selected from the group consisting of amino, isocyanato (—N=C=O), isothiocyanato (—N=C=S), —NH—C(=O)—X or —NH—C(=S)—X;

$R^8$ is alkyl ($C_1$–$C_{20}$), —$(CH_2)_m$—Ar, or polyhydroxyalkyl ($C_1$–$C_{20}$);

n is 1 or 2;

m is 1 to 15;

X is a targeting moiety; and

Ar is phenyl optionally substituted with one, two or three substituents selected from the group consisting of amino, acylamino, hydroxy, alkyl (C1–C5) and halogen.

23 Claims, No Drawings

CYCLIC TRIAMINE CHELATING AGENTS

FIELD OF THE INVENTION

The present invention relates to novel cyclic triamine compounds useful as chelating agents for magnetic resonance imaging and in other diagnostic and therapeutic applications.

BACKGROUND OF THE INVENTION

Magnetic resonance (MR) is widely used for obtaining spatial images of human subjects for clinical diagnosis. A review of this technology and clinical applications is provided by D. P. Swanson et al., in *Pharmaceuticals in Medical Imaging*, 1990, Macmillan Publishing Company, pages 645–681.

MR images are a composite of the effects of a number of parameters which are analyzed and combined by computer. Choice of the appropriate instrument parameters, such as radio frequency (Rf), pulsing and timing can be utilized to enhance or attenuate the signals of any of the image-producing parameters thereby improving image quality and providing better anatomical and functional information. In many cases, MR imaging has proven to be a valuable diagnostic tool, as normal and diseased tissue, by virtue of their possessing different parameter values, can be differentiated in the image.

In MR imaging, the in vivo image of an organ or tissue is obtained by placing the body of a subject in a strong external magnetic field, pulsing with radio frequency energy, and observing the effect of the pulses on the magnetic properties of the protons contained in and surrounding the organ or tissue. A number of parameters can be measured. The proton relaxation times, $T_1$ and $T_2$, are of primary importance. $T_1$, also called the spin-lattice or longitudinal relaxation time, and $T_2$, also called the spin-spin or transverse relaxation time, depend on the chemical and physical environment of the organ or tissue water and are measured using Rf pulsing techniques. This information is analyzed as a function of spatial location by computer which uses the information to generate an image.

Often the image produced hicks appropriate contrast, e.g., between normal and diseased tissue, reducing diagnostic effectiveness. To overcome this drawback, contrast agents have been used. Contrast agents are substances which exert an effect on the MR parameters of various chemical species around them. Theoretically, a contrast agent, if taken up preferentially by a certain portion of an organ or a certain type of tissue, e.g., diseased tissue, can provide contrast enhancement in the resultant images.

Inasmuch as MR images are strongly affected by variations in the $T_1$ and $T_2$ parameters, it is desirable to have a contrast agent which effects either or both parameters. Research has focused predominantly on two classes of magnetically active materials, i.e., paramagnetic materials, which act primarily to decrease T1, and superparamagnetic materials, which act primarily to decrease $T_2$.

Paramagnetism occurs in materials that contain unpaired electrons. Paramagnetic materials are characterized by a weak magnetic susceptibility (response to an applied magnetic field). Paramagnetic materials become weakly magnetic in the presence of a magnetic field and rapidly lose such activity, i.e., demagnetize, once the external field has been removed. It has long been recognized that the addition of paramagnetic solutes to water causes a decrease in the $T_1$ parameter.

Paramagnetic materials, for example, gadolinium (Gd) containing materials, have been used as MR contrast agents primarily because of their effect on $T_1$. Gd has the largest number of unpaired electrons (seven) in its 4f orbitals and exhibits the greatest longitudinal relaxivity of any element.

A major concern with the use of contrast agents for MR imaging is that many paramagnetic materials exert toxic effects on biological systems making them inappropriate for in vivo use. For example, the free form of Gd is quite toxic. To make it suitable for in vivo use, researchers have chelated it with diethylenetriaminepentaacetic acid (DTPA). A formulation of this material that has undergone extensive clinical testing consists of Gd-DTPA neutralized with two equivalents of N-methyl-D-glucamine (meglumine). This agent has been successful in enhancing human brain and renal tumors.

Despite its satisfactory relaxivity and safety, this formulation has several disadvantages. For example, due to its low molecular weight, Gd-DTPA dimeglumine is cleared very rapidly from the blood stream and tissue lesions (tumors). This limits the imaging window, the number of optimal images that can be taken after each injection, and increases the agents required dose and relative toxicity. In addition, the biodistribution of Gd-DTPA is suboptimal for imaging body tumors and infections due to its small molecular size.

Several approaches have been taken in attempts to overcome these disadvantages. For example, Gd and Gd-chelates have been chemically conjugated to macromolecular proteins such as albumin, polylysines and immunoglobulins. Drawbacks of conjugating DTPA to protein carriers for use in MR image enhancement include inappropriate biodistribution and toxicity. In addition, proteins provide a defined platform not subject to wide synthetic variation. Moreover, thermal sterilization of protein conjugates tends to be problematic, especially in the case of albumin conjugates, since the high heat needed for sterilization denatures protein and can degrade the conjugates.

U.S. Pat. No. 5,021,571 issued Jun. 4, 1991 to Mease et al. discloses cyclohexyl EDTA (ethylenediaminetetraacetic acid) and its monoanhydride, useful as a chelating agent which can be linked with an antibody and chelated with a radiometal to form an immunoconjugate. In view of the drawbacks of other contrast media, it is readily apparent that new and/or better MR contrast media are needed. The present invention is directed to this, as well as other, important ends.

SUMMARY OF THE INVENTION

The present invention provides compounds of the formula

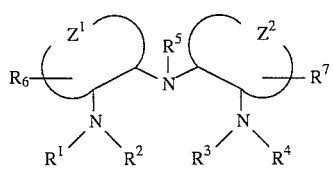

Formula I wherein $Z^1$ and $Z^2$ each represent the atoms necessary to complete a monocyclic or polycyclic carbocyclic or heterocyclic ring system, said $Z^1$ and $Z^2$ independently optionally substituted with $R^6$ and $R^7$, respectively;

$R^1$, $R^2$, $R^3$ and $R^4$ are independently carboxyalkyl $(C_1-C_2)$, $-(CH_2)_n-C(=O)-NH-R^8$, or $-(CH_2)_n-C(=O)-O-R^8$, $R^5$ is carboxyalkyl ($C_1$–$C_2$);

$R^6$ and $R^7$ are independently hydrogen, benzyl, or benzyloxy, said benzyl or benzyloxy optionally substituted with one, two or three substituents selected from the group consisting of amino, isocyanato (—N=C=O), isothiocyanato (—N=C=S), —NH—C(=O)—X or —NH—C(=S)—X;

$R^8$ is alkyl ($C_1$–$C_{20}$), —$(CH_2)_m$—Ar, or polyhydroxyalkyl ($C_1$–$C_{20}$);

n is 1 or 2;

m is 1 to 15;

X is a targeting moiety; and

Ar is phenyl optionally substituted with one, two or three substituents selected from the group consisting of amino, acylamino, hydroxy, alkyl ($C_1$–$C_5$) and halogen.

The compounds of the invention can be chelated with a metal ion and used as contrast agents for magnetic resonance imaging and for other applications. The present invention also provides pharmaceutical compositions comprising a compound of the invention and a pharmaceutically acceptable carrier or diluent. The invention further provides methods of providing an image of an internal region of a patient comprising administering to a patient a compound of the invention and scanning the patient using magnetic resonance imaging to obtain visible images of the region.

The present invention is more particularly pointed out in the appended claims and is described in its preferred embodiments in the following description.

DETAILED DESCRIPTION OF THE INVENTION

The present invention provides novel compounds of Formula I as defined herein useful as contrast agents for MR imaging and for other applications as described hereinafter. The compounds of the invention, when chelated with a paramagnetic metal ion to form MR contrast agents, provide good images of the liver and kidney and can also be used to provide images of other organs and/or tissues.

In the compounds of Formula I, $Z^1$ and $Z^2$ each preferably represent the atoms necessary to complete a monocyclic, bicyclic or tricyclic ring system, which ring system can be carbocyclic or heterocyclic. As used herein, carbocyclic refers to saturated, partially unsaturated and aromatic ring systems having from 3 to about 10 carbon atoms if monocyclic, up to about 20 carbon atoms if polycyclic. As used herein, polycyclic refers to ring systems containing two or more component rings. Polycylic ring systems can be fused (i.e. sharing two or more carbon atoms with at least one other component ring, or directly joined by single or double bonds. Exemplary monocyclic carbocyclic ring systems include cyclobutane, cyclopentane, cyclohexane, cycloheptane, cyclooctane, benzene and cyclohexene. A preferred monocyclic carbocyclic ring system is cyclohexane. More preferably $Z^1$ and $Z^2$ each represent the atoms necessary to complete a cyclohexane ring system. Exemplary bicyclic carbocyclic ring systems include naphthalene, indene, azulene, biphenyl, biphenylene and cyclohexylbenzene. Exemplary tricyclic carbocyclic ring systems include phenanthrene, anthracene, and indacene. Heterocyclic ring systems contain one or more heteroatoms, or combination of different heteroatoms, such as O, N, S, or Si. Suitable monocyclic heterocyclic rings systems include ring systems such as pyridine, furan, thiophene and isoxazole. Exemplary bicyclic heterocyclic ring systems include indole, quinoline, chroman and pteridine. Exemplary tricyclic heterocyclic ring systems include xanthene, carbazole, acridine and phenorazine.

$R^1$, $R^2$, $R^3$ and $R^4$ are preferably independently carboxyalkyl ($C_1$–$C_2$), i.e. —$(CH_2)_p$—C(=O)—OH, where p is 1 or 2, more preferably carboxymethyl. In other embodiments of the invention, $R^1$, $R^2$, $R^3$ and $R^4$ can also be independently selected to be the amide or ester of the aforementioned compounds, i.e. —$(CH_2)_n$—C(=O)—NH—$R^8$, or —$(CH_2)_n$—C(=O)—O—$R^8$, where $R^8$ is as defined hereinabove. n is 1 or 2, preferably 1.

$R^5$ is carboxyalkyl ($C_1$–$C_2$), preferably carboxymethyl.

$R^6$ and $R^7$ are independently hydrogen, benzyl or benzyloxy substituted with one, two or three substituents selected from the group consisting of amino, isocyanato (—N=C=O), isothiocyanato (—N=C=S), —NH—C(=O)—X or ≦NH—C(=S)—X, where X is a targeting moiety. Preferably $R^6$ and $R^7$ are independently hydrogen, substituted benzyl or substituted benzyloxy.

X can be selected from a wide variety of naturally occurring or synthetically prepared materials, including, but not limited to, enzymes, amino acids, peptides, polypeptides, proteins, lipoproteins, glycoproteins, lipids, phospholipids, hormones, growth factors, steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies (monoclonal and polyclonal), anti-antibodies, antibody fragments, antigenic materials (including proteins and carbohydrates), avidin and derivatives thereof, biotin and derivatives thereof and others known to one skilled in the art. X is preferably an antibody or antibody fragment. Preferred antibodies or fragments include antibodies or antibody fragments capable of targeting the compound of the invention to a specific tissue or location in the body, for example, those specific for tumor-associated antigens such as B72.3 which recognizes colorectal tumors, 9.2.27 and related anti-melanoma antibodies, D612 and related antibodies which recognize colorectal tumors, UJ13A and related antibodies which recognize small cell lung carcinomas, NRLU-10, NRCO-02 and related antibodies which recognize small cell lung carcinomas and colorectal tumors (Pan-carcinoma); 7E11C5 and related antibodies which recognize prostate tumors; CC49 and related antibodies which recognize colorectal tumors; TNT and related antibodies which recognize necrotic tissue, PR1A3 and related antibodies which recognize colon carcinoma; ING-1 and related antibodies which are described in International Patent Publication WO-A-90/02569; B174, C174 and related antibodies which recognize squamous cell carcinomas; B43 and related antibodies which are reactive with certain lymphomas and leukemias; and anti-HLB and related monoclonal antibodies. These particular embodiments of the invention should be particularly useful for imaging of tumors that express tumor-specific antigens, or for radiotherapy of tumors. The targeting moiety can be attached to the compounds by conventional reactions, for example, through the amino, isocyanato or thiocarbonyl groups of the compounds of the invention and the carboxyl, aldehyde or amino groups on the antibody or antibody fragment.

$R^8$ can be $C_1$–$C_{20}$ saturated or unsaturated, straight chain or branched alkyl, preferably $C_1$ to about $C_{10}$ alkyl, more preferably $C_1$ to about $C_5$ alkyl. $R^8$ can also be —$(CH_2)_m$—Ar or polyhydroxyalkyl. Ar is phenyl optionally substituted with one, two or three substituents selected from the group consisting of amino, acylamino (R'—C(=O)—NH—, wherein R' is alkyl $C_1$–$C_4$), hydroxy, alkyl ($C_1$–$C_5$) and halogen. Preferably the phenyl is optionally substituted with one substituent. m is an integer from 1 to 15; preferably from 1 to about 10, more preferably from 1 to about 5. Polyhydroxyalkyl ($C_1$–$C_{20}$) refers to straight or branched chain, saturated or unsaturated alkyl having from 1 to about 20 carbon atoms, preferably from 1 to about 10 carbon atoms and substituted with 2 or more hydroxyl groups, depending on the length and degree of saturation of the alkyl chain. The $R^8$ groups can be chosen to control the solubility, hydrophilicity and other properties of the compounds of the invention and can be used to regulate various actions of the chelated compounds upon administration. Such action may include the chelate's biodistribution, metabolism, clearance or other biochemical interations or the lack thereof. For example, if $R^8$ is chosen to be a more lipophilic group such as a longer chain alkyl or aryl, the resulting compounds would increase the lipid solubility of contrast media prepared from such compounds and consequently its biodistribution once administered.

The carboxy portion (—C(=O)—OH) of the carboxyalkyl groups of $R^1$, $R^2$, $R^3$, $R^4$ and $R^5$ can be in the form of an acid anhydride and such forms are intended to be literally encompassed within the term carboxy. A preferred type of anhydride includes the internal anhydrides formed between the carboxy portions of $R^1$ and $R^2$ or $R^3$ and $R^4$. Also encompassed within the term carboxy is the —C(=O)—O⁻ form. Salts of the compounds such as the trifluoroacetic acid salt or a halogen salt, such as the sodium salt, are also within the scope of the invention.

A preferred compound of the invention is dicyclohexylenetriaminepentaacetic acid (DCTPA) (Formula I wherein $Z^1$ and $Z^2$ each represent the atoms necessary to form a cyclohexane ring, and $R^1$, $R^2$, $R^3$, $R^4$ and $R^5$ are each carboxymethyl).

The compounds can be used to form polymeric contrast agents as described in published PCT application WO 93/06148. In published PCT application WO 93/06148, polynitrilo chelating agents are reacted with monomers such as ethylene glycol or polyethylene glycol to form polymers. The polymers thus formed can then be chelated with a metal ion and employed as described herein for the compounds of the invention. The compounds of the invention can be substituted for the polynitrilo chelating agents disclosed therein to form the polymers.

The compounds of the present invention can be produced by a number of generalized methods. The following schemes represent possible methodologies for preparation of the compounds of the invention but not intended to be limiting as other methodologies are also possible.

In Scheme A, an amine or sulfonamide is used to open two equivalents of an aziridine derivative to form a symmetrical derivative ($Z^1=Z^2$, $R^6=R^7$) which is further elaborated into the final product.

Scheme A

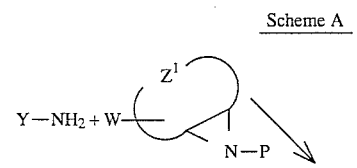

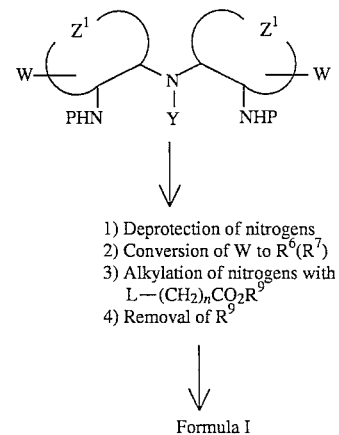

Y = akyl, aralkyl or arylsulfonyl
W = $R^6$($R^7$) or protected precursor to $R^6$($R^7$)
$R^9$ = t-butyl, benzyl
L = leaving group
P = protecting group In Scheme B, a diamine or monoprotected diamine is used to open an aziridine derivative to form a symmetrical or asymmetrical derivative which is further elaborated into the final product.

Scheme B

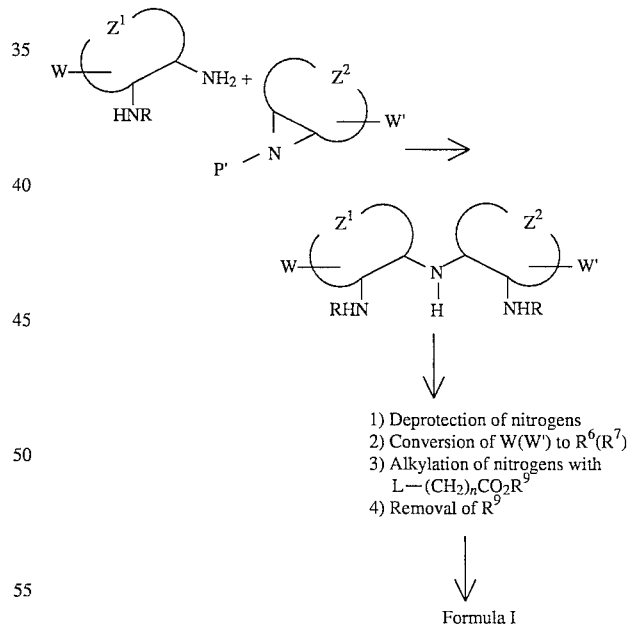

P' = Protecting group
R = H or protecting group
W = $R^6$ or protected precursor to $R^6$
W' = $R^7$ or protected precursor to $R^7$
L = leaving group
$R^9$ = t-butyl or benzyl In Scheme C, an amine or sulfonamide is used to open epoxide derivatives to form a dihydroxyamino derivative which is converted to a triamine and further elaborated to the final product.

Scheme C
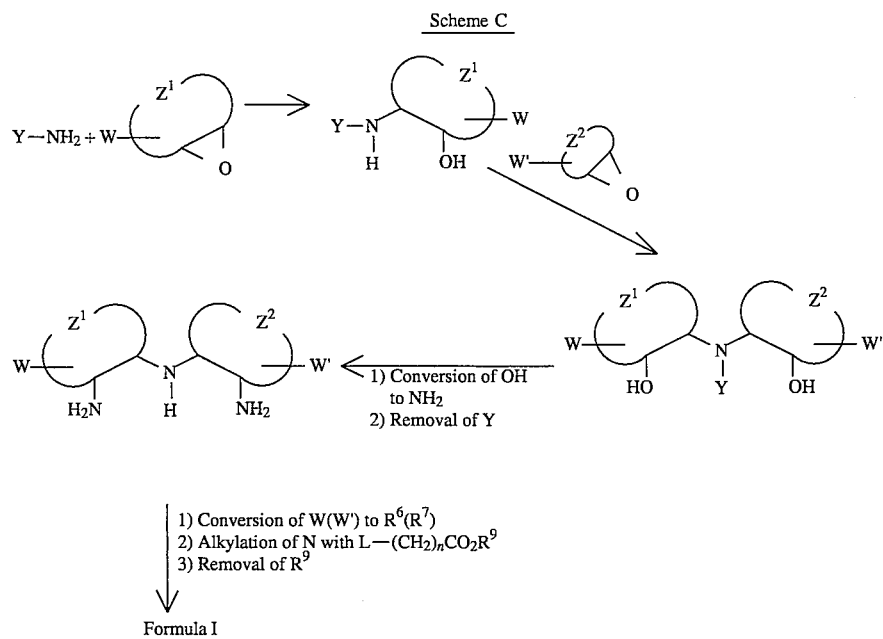
When both rings are aromatic, the following methodology of Scheme D may be employed. In Scheme D, $Z^1$ and $Z^2$ can be the same or different.
Scheme D
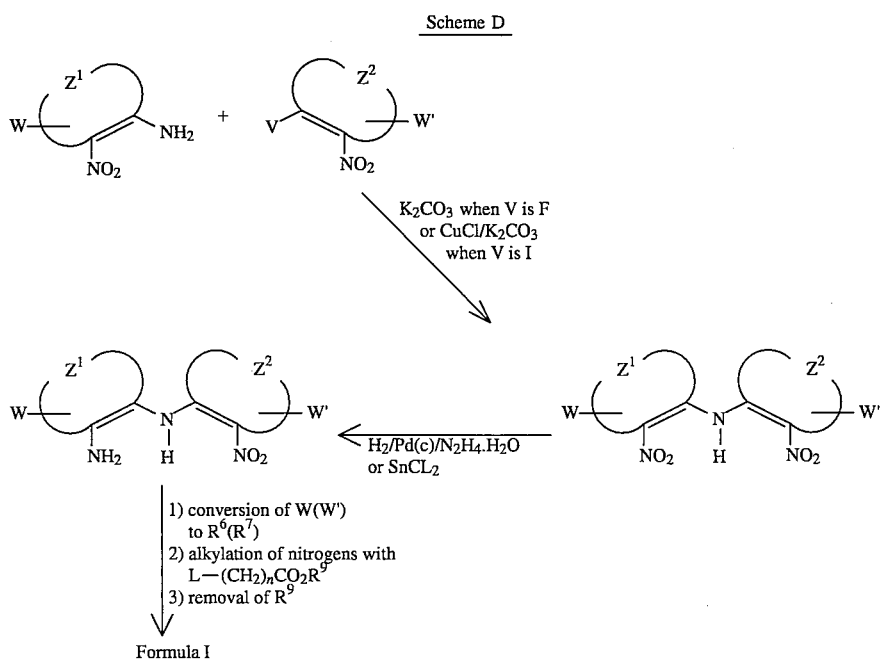
W = $R^6$ or protected precursor to $R^6$
W' = $R^7$ or protected precursor to $R^7$
V is iodine or fluorine
$R^9$ is t-butyl or benzyl A preferred embodiment of the invention, dicyclohexylenetriaminepentaacetic acid (DCTPA) (5) (and gadolinium complex (6)) and its isomer DCTPA' (8) (and gadolinium complex (9)) can be prepared according to the method shown in synthetic Scheme I which uses the methodology represented in Scheme B.

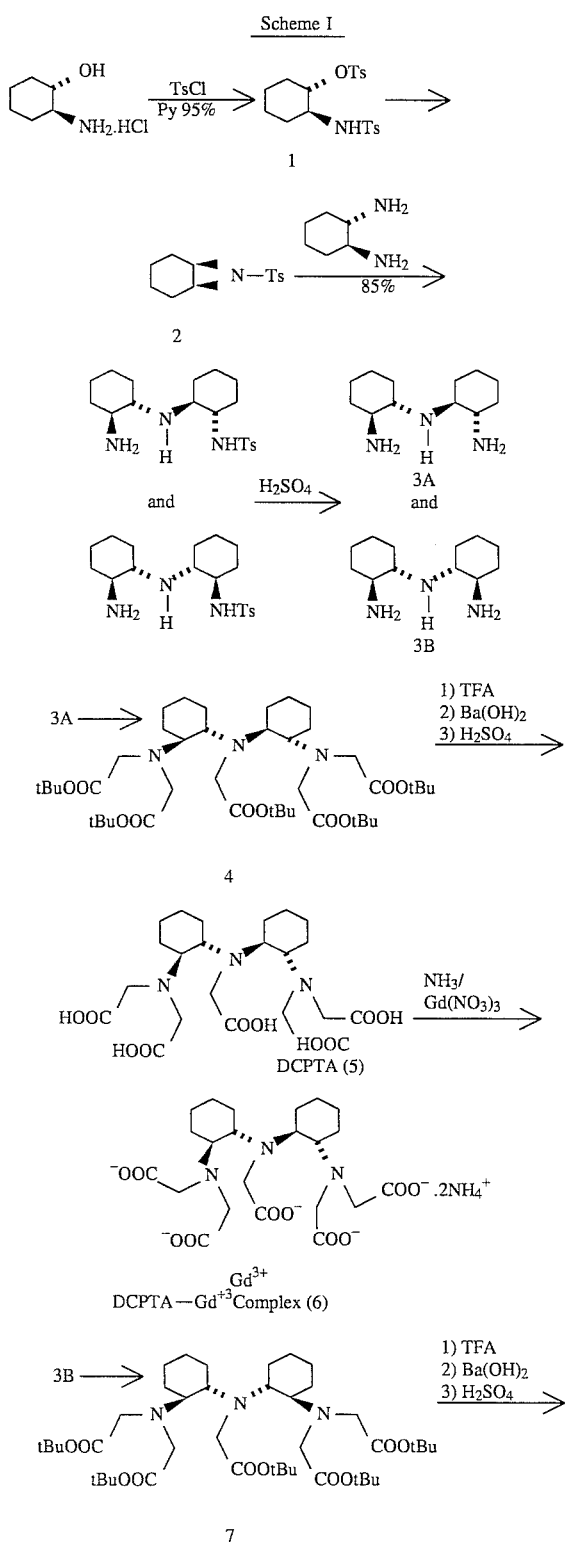

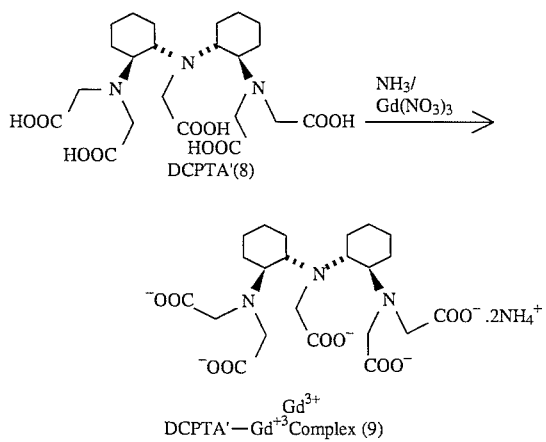

-continued
Scheme I

Abbreviations:
Ts-p-toluenesulfonyl(tosyl); Py-pyridine; tBu-t-butyl; TFA-trifluoroacetic acid The compounds of the invention can be chelated with metal ions using conventional techniques. For example, an aqueous solution of the compound of the invention can be mixed with the salt of the desired metal (radionuclide, paramagnetic metal, etc.), generally at a pH of from about 4 to about 11, preferably at a pH of from about 5 and about 9. The salt can be any salt of the metal, preferably a water soluble salt, such as a halogen salt, or the citrate or nitrate salt. Buffers such as acetate, phosphate and borate can optionally be added to the aqueous solution to produce the optimum pH for chelation of the compound with the metal ions.

The present invention is useful in imaging a patient generally, and/or in specifically diagnosing the presence of diseased tissue in a patient. The imaging process of the present invention may be carried out by administering a compound of the invention with a chelated paramagnetic ion (a contrast agent of the invention) to a patient, and then scanning the patient using magnetic resonance imaging to obtain visible images of an internal region of a patient and/or of any diseased tissue in that region. By region of a patient, it is meant the whole patient or a particular area or portion of the patient. The contrast agents of the invention can be used for providing images of the vasculature, gastrointestinal tract, the liver, kidney, bladder, and heart, as well as other regions of the body. The patient can be any type of animal, bird, etc., although usually the patient will be a human patient or a mammalian species commonly used in laboratory experiments, such as a dog, rat, or mouse.

Exemplary paramagnetic ions suitable for use in the subject invention for magnetic resonance imaging include transition, lanthanide (rare earth) and actinide elements, as will be readily apparent to those skilled in the art, in view of the present disclosure. The paramagnetic element can be selected from elements of atomic number 21–29, 43, 44 and 57 to 71. Preferable elements include Cr, V, Mn, Fe, Co, Ni, Cu, La, Ce, Pr, Nd, Pm, Sm, Eu, Gd, Tb, Dy, Ho, Er, Tin, Yb, and Lu. More preferably the elements include Mn, Gd, and Dy, most preferably Gd.

The dosages of the contrast agent used according to the method of the present invention will vary according to the precise nature of the contrast agent used. Preferably however, the dosage should be kept as low as is consistent with achieving contrast enhanced imaging and volumes minimized for IV drip or bolus injection. In this way, the toxicity potential is minimized. For most MR contrast agents the appropriate dosage will generally range from about 0.005 to about 5.0 millimoles paramagnetic metal/kg body weight, preferably from about 0.01 to about 1.0 millimoles paramagnetic metal/kg body weight, more preferably from about 0.025 to about 0.2 millimoles paramagnetic metal/kg body weight. It is well within the skill of the average practitioner in this field to determine the optimum dosage for any particular MR contrast agent by relatively routine experimentation, for both in vivo or in vitro applications.

Administration may be carried out in various fashions, such as intravascularly, orally, rectally, etc., using a variety of dosage forms. The useful dosage to be administered and the particular mode of administration will vary depending upon the age, weight and the particular mammal and region to be scanned. Typically, dosage is initiated at lower levels and increased until the desired contrast enhancement is achieved. By way of general guidance the amounts described above can be used, taking into consideration the chelating agent and any targeting moiety, although higher and lower amounts can be employed. Various combinations of chelating agents and paramagnetic ions may be used to modify the relaxation behavior of the contrast agent. In carrying out the method of the present invention, the contrast medium can be used alone, or in combination with other diagnostic, therapeutic or other agents.

The magnetic resonance imaging techniques which are employed in the methods of the invention are conventional and are described, for example, in D. M. Kean and M. A. Smith, *Magnetic Resonance Imaging: Principles and Applications,* (William and Wilkins, Baltimore 1986) and Swanson et al., supra.. Contemplated MRI techniques include, but are not limited to, nuclear magnetic resonance (NMR) and electronic spin resonance (ESR). The preferred imaging modality is NMR.

In addition to their use in MR imaging, the compounds of the invention can be used to bind shift reagents (e.g., Dy(III)), or relaxation agents, (e.g., Gd(III)), as well as mixtures thereof (e.g., Dy(III) with Gd(III), and thus have applications in magnetic resonance spectroscopy.

The compounds of the invention are also useful as x-ray and ultrasound contrast agents, for nuclear medicine as imaging agents, and for radiotherapy, with administration being carried out as described above. For x-ray and ultrasound, the compounds may be employed to chelate heavy metals such as Hf, La, Yb, Dy, Gd and Pb. For nuclear medicine, the compounds may be employed to chelate radioactive metals, in particular the radioisotopes of Sc, Fe, Pb, Ga, Y, Bi, Mn, Cu, Cr, Zn, Ge, Mo, Tc, Ru, In, Sn, Sr, Sm, Lu, Sb, W, Re, Po, Ta, and Tl. Preferred radionuclides include $^{44}$Sr, $^{64}$Cu, $^{67}$Cu, $^{111}$In, $^{212}$Pb, $^{68}$Ga, $^{87}$Y, $^{90}$Y, $^{153}$Sm, $^{212}$Bi, $^{99m}$Tc, $^{177}$Lu, $^{186}$Re, and $^{188}$Re. More preferably the radionuclide is $^{90}$Y. These radioisotopes can be atomic or preferably ionic.

For use as local radiation sensitizers for radiation therapy, the compounds may chelate radioactive metals such as those described above, and optionally a variety of heavy metals and lanthanide (rare earth) metals as described above. In this regard, the selection of heavy metals and rare earths may be done to match the energy absorption spectrum of the incident radiation and increase conversion of Auger electrons, high energy particles and emission of secondary radiation.

For use in fluorescence spectroscopy and as a marker in assays such as immunoassays, the compounds of the invention may chelate a fluorescent metal ion selected from metals of atomic number 57 to 71. Ions of the following metals are preferred: La, Ce, Pr, Nd, Pm, Sm, Eu, Gd, Tb, Dy, Ho, Er, Tm, Yb, and Lu. Eu. is a preferred fluorescent metal ion.

Additionally, the compounds of the invention may be used to treat heavy metal poisoning, e.g., for iron, arsenic or lead poisoning. For treatment of heavy metal poisoning, the compounds will generally be administered alone without chelated ions, although as one skilled in the art will recognize, in some applications of metal poisoning treatment, some calcium or other metal ions may be added to the formulation of the compounds prior to administration. Otherwise, administration may be carried out as described above. The compounds of the invention may be used to treat poisoning from such metal ions as Mg, Ca, Sc, Ti, V, Cr, Mn, Mg, Fe, Eu, Er, Pb, Co, Ni, Cu, Zn, Ga, Sr, Y, Zr, Tc, Ru, In, Hf, W, Re, Os, Pb, Bi, Dy, Mn, Gd, Hf, La, Yb, Tc, In and As.

Additionally, the compounds of the invention may be chelated to a metal and used as therapeutic agents to treat metal deficiencies, with administration being carried out as described above. Metal ions which may be bound to the compounds for treatment of deficiency include Mn, Fe, Zn, Co, Ni, Cu, Cr, Mg, Se and Ca.

The pharmaceutical compositions of the invention can be formulated, for use as contrast agents or other use as described herein, with the compounds of the invention and conventional pharmaceutical or veterinary carriers or diluents and can also contain other conventional agents, such as, for example, stabilizers, antioxidants, osmolality adjusting agents, buffers, pH adjusting agents, etc. Depending on the particular end use, the pharmaceutical compositions can be formulated with the compound of the invention in chelated or unchelated form. For some uses, it may be preferable to supply the pharmaceutical compositions with the compound of the invention in unchelated form and add the metal ion to the pharmaceutical composition just prior to actual use, allowing time for the metal ion to chelate with the compound of the invention.

The pharmaceutical compositions can be in a form suitable for injection or infusion directly or after dispersion in or dilution with a physiologically acceptable carrier medium, e.g., water for injection. Thus, the pharmaceutical compositions may be formulated in conventional administration forms such as powders, solutions, suspensions, dispersions, etc., however solutions, suspensions and dispersions in physiologically acceptable carrier media will generally be preferred.

The pharmaceutical compositions may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

Parenterally administrable forms, e.g., intravenous solutions, should, of course, be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405– 1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

The present invention is further described in the following examples which are not intended in any way to limit the scope of the invention.

EXAMPLES

Example 1

Synthesis of Dicyclohexylenetriaminepentaacetic Acid (DCTPA) (5)

A. Trans-2-N-Tosylamide cyclohexyl tosylate (1): To a stirred suspension of trans -2-amino cyclohexanol hydrochloride 75 g (0.49 mol, Aldrich Chemical Co., Milwaukee, Wis.) in anhydrous pyridine at 0° C. was added 200 g (1.05 mol) of p-toluenesulfonyl chloride. The resulting mixture was stirred at room temperature for 48 hrs and then poured into ice (1000 g). After stirring for 2 hrs, a yellow solid was filtered and washed with water (2×500 ml) and ethanol (200 ml). The solid was dried under vacuum for 24 hrs to give 1 as a slightly yellow solid (192 g, 92%); mp 160–162° C.; $^1$H NMR (360 MHz, CDCl$_3$)δ:7.70 (d, 4H, J=7.9, Ar—H), 7.30 (d, 2H, J=7.9, Ar—H), 7.23 (d, 2H, J=7.9, AR—H), 4.98 (d, 1H, J=5.6, NH), 4.24 (m, 1H, CH —O), 3.12 (m, 1H, CH —N), 2.43 (s, 3H, CH$_3$), 2.39 (s, 3H, CH$_3$), 2.12-1.18 (m, 8H); $^{13}$C NMR (300 MHz, CDCl$_3$)δ: 145.60, 143.88, 137.97, 130.45, 130.18, 128.44, 127.76, 81.48, 55.65, 32.32, 31.10, 23.32, 22.10; HRMS (PK match, LSIMS, CH$_2$Cl$_2$—MeOH) calc'd for C$_{22}$H$_{25}$NO$_5$S$_2$ (M+H)$^+$ 424.12524, found (M+H)$^+$ 424.12353. Elemental Analysis Calc. for C$_{22}$H$_{25}$NO$_5$S$_2$·H$_2$O: C, 56.76; H, 5.85; N, 3.01; found, C, 56.82; H, 6.00; N, 3.29.

B. N-Tosyl cyclohexyl aziridine (2): To a suspension of sodium hydride (20 g, 0.833 mol) in dry. tetrahydrofuran (THF) (500 ml) was added trans-2-N-tosylamide cyclohexyl tosylate 1 (190 g, 0.449 mol) portionwise at room temperature. After evolution of hydrogen ceased, the mixture was filtered and the precipitate was washed with THF. The combined organic liquor was evaporated to give 2 as a yellow solid (105.5 g, 94%); mp 59 61° C.; $^1$H NMR (360 MHz, CDCl$_3$) δ:7.68 (d, 2H, J=8.2, Ar—H), 7.28 (d, 2H, J=8.2, Ar—H), 2.92 (d, 2H, J=10, CH—N), 2.39 (s, 3H, CH$_3$), 1.74 (m, 4H, CH$_2$), 1.35 (m, 2H, CH$_2$), 1.18 (m, 2H, CH$_2$); $^{13}$C NMR (300 MHz, CDCl$_3$) δ: 144.58, 130.12, 128.09, 40.31, 23.30, 22.10, 19.94; HRMS (PK match, LSIMS, CH$_2$Cl$_2$—MeOH) calc'd for C$_{13}$H$_{17}$NO$_2$S (M+H)$^+$ 252.10583, found (M+H)$^+$ 252.10592. Elemental Analysis Calc'd for C$_{13}$H$_{17}$NO$_2$S, C, 62.12; H, 6.82; N, 5.57; found, C, 61.90; H, 6.90; N, 5.62.

C. Di-(N-trans-2'-aminocylohexyl)amine (3A and 3B): To a refluxing solution of (+/−)-trans-1,2-diaminocyclohexane (100 ml, 0.833 mol) in anhydrous acetonitrile (200 ml) was slowly added 35 g (0.139 mol) of N-tosyl cyclohexylaziridine 2 in acetonitrile (50 ml). After the addition was complete, the solution was refluxed for 2 hours. The solvent was removed and excess trans-1,2-diaminocyclohexane was distilled under vacuum. The resulting oil was titrated with hexane to give pale yellow solid (43 g, 84%), which was used in the next step without further purification. The above solid (43 g) was heated to 100°–110° C. with 98% conc. H$_2$SO$_4$ (200 ml) for 20 hrs. The resultant solution was cooled with salt-ice bath and ether was added slowly with stirring to keep the temperature below 10° C. More ether was added until no further precipitation occurred. The precipitate was filtered and washed with ether under nitrogen. The grey solid was redissolved in a small amount of water (10 ml) and concentrated (60%) sodium hydroxide was added to make the solution basic. The basic aqueous solution was extracted with ether (5×100 ml). Drying and evaporation of the ether solution provided a mixture of 3B and 3A as a pale yellow solid. The mixture was separated by flash chromatography (CH$_2$Cl$_2$/CH$_3$OH saturated with NH$_3$ (g): 7/3) to provide compound 3A, 9.0 g (31%) and compound 3B, 2.5 g (9%); 3A, mp 104°–106° C.; $^1$H NMR (360 MHz, CDCl$_3$) δ: 2.26 (m, 1H), 2.24 (m, 2H), 1.95 (m, 1H), 1.63 (m, 3H), 1.39 (m, 5H), 1.23-1.06 (m, 6H), 0.90-0.83 (m, 2H); $^{13}$C NMR (300 MHz, CDCl$_3$), δ: 60.64, 55.97, 36.87, 32.79, 25.86; HRMS (PK match, LSIMS, CH$_2$Cl$_2$-MeOH) calc'd for C12H25N3 (M+ H)$^+$212.21267, found (M+ H)$^+$212.21181; 3B, mp 56°–58° C.; $^1$H NMR (360 MHz, CDCl$_3$) δ:2.21 (m, 2H), 1.96 (m, 2H), 1.80 (m, 4H), 1.51 (m, 6H), 1.09–0.85 (m, 6H); $^3$C NMR (300MHz, CDCl$_3$) δ: 64.59, 57.49, 35.40, 34.93, 26.19, 25.51; HRMS (PK match, LSIMS, CH$_2$Cl$_2$-MeOH) calc'd for C$_{12}$H$_{25}$N$_3$ (M+ H)$^+$212.21267, found (M+H)$^+$ 212.21282.

D. t-Butyl Dicyclohexylenetriaminepentaacetic Acid (t-butyl DCTPA) (4): A mixture of the dicyclohexenetriamine 3A (18.5 g, 87.6 mmol), t-butyl bromoacetate (100 ml, 615 mmol), anhydrous potassium carbonate (67 g, 613 mmol), and molecular sieves (4Å, 60 g) in anhydrous acetonitrile (500 ml) was stirred at 50° C. for 35 hrs. The precipitate was filtered off, and the solution was evaporated under vacuum to remove solvent and excess t-butyl bromoacetate. The resulting oil was dissolved in isopropyl alcohol and the solution was kept at −18° C. to −20° C. After 2 days, white crystals were collected and washed with isopropanol to give 15.8 g of 4; The mother liquor was cooled to −20° C. and after 1 week, a second crop of 4(15.7 g) was obtained. Total: 31.5 g (46%); mp 106°–107.5° C.; $^1$H NMR (360 MHz, CDCl$_3$) δ:3.50–3.61 (m, 10 H), 2.71 (m, 2H, CH -N), 2.54 (m, 2H, CH—N), 2.04 (m, 4H), 1.61 (m, 4H), 1.46 (s, 49H, CH$_3$), 1.19–1.05 (m, 8H); $^{13}$C NMR (300MHz, CDCl$_3$) δ: 173.96, 172.47, 80.59, 80.17, 65.73, 64.31, 54.05, 47.58, 31.98, 29.81, 28.75, 26.47; HRMS (PK match, LSIMS, CH$_2$Cl$_2$-MeOH) calc'd for C$_{42}$H$_{72}$N$_2$O$_{10}$ (M+H)$^+$782.55307, found (M+H)$^+$ 782.55664.

E. Dicyclohexylenetriaminepentaacetic Acid (DCTPA) (5): 4(15.0 g, 19 mmol) was stirred in trifluoroacetic acid (TFA) (20 ml) for 15 hrs. The TFA was evaporated and dried under vacuum to give an oil which was titrated with hexane to give a white solid (15.3 g). Elemental analysis of this crude product showed that it contains approximately 2 to 3 equivalents of TFA. Purification of the crude product was performed according to the following procedure: The crude product 1.5 g in water (3 ml) was neutralized by sat. Ba(OH)$_2$ to pH 8 and warmed for 30 minutes. The slurry was filtered and washed with water. The precipitate was suspended in water (5 ml) and the pH adjusted to 2 with 20% H$_2$SO$_4$. The suspension was stirred at 80° C. overnight (adjusted pH to 2 with aqueous barium hydroxide/dilute sulfuric acid). The precipitate was filtered and aqueous flitrate was evaporated and dried to provide 5 as a white solid (0.75 g, 80%). mp 170° C. (dec.); $^1$H NMR (360 MHz, DMSO-d$_6$) δ:3.78 (d, 1H, J = 48.6, N—CH—CO), 3.73 (d, 1H, J=48.6, N—CH—CO), 3.62 (d, 4H, J=41.8, N—CH—CO), 3.56 (d, 4H, J=41.8, N—CH—CO), 3.17 (m, 2H), 2.87 (m, 2H), 2.33 (m, 2H), 1.61 (m, 4H), 1.31– 1.12 (m, 8H); $^{13}$C NMR (360 MHz, DMSO-d$_6$) δ: 178.46, 176.17, 71.40, 69.03, 53.32, 34.66, 32.61, 32.55, 30.51, 30.35. HRMS (PK match, LSIMS, MeOH/DMSO) calc'd $C_{22}H_{35}N_3O_{10}$ $(M+H)^+$502.24007, found $(M+H)^+$502.24077; Elemental Analysis calc'd for $C_{22}H_{35}N_3O_{10} \cdot H_2O$: C, 50.86; H, 7.18, C, 8.09; found, C, 51.29; C, 7.12, H, 8.12.

Example 2

Gadolinium Complex of DCTPA (6)

3 g of above crude product (DCTPA (5-TFA salt) was dissolved in isopropanol (10 ml) and saturated with anhydrous ammonia (excess) by bubbling gaseous ammonia through the solution for 15 minutes. The resultant white precipitate was filtered and washed with isopropanol. The obtained white powder (3.1 g) was dissolved in deionized water (5 ml). Gadolinium nitrate (2.5 g) in deionized water (5 ml) was added slowly to the above aqueous solution. The reaction was monitored by PAR (4-(2-pyridylazo)resorcinol monosodium salt) test. The addition of gadolinium nitrate was stopped when the PAR reagent indicated the presence of unchelated $Gd^{3+}$. After the addition, the solution was adjusted to pH 7 with ammonium hydroxide/nitric acid. Acetone was added until the solution became cloudy, and the suspension was cooled to 4° C. After 2 days, the resulting white precipitate was filtered and washed with acetone. The white solid (6) was dried at 80° C. under vacuum for 2 days to provide pale yellow solid (3.10 g, 71%); mp 220° C. (dec.). Elemental Analysis calc'd for $C_{22}H_{38}N_5O_{10}Gd \cdot 3H_2O$: C, 35.52; H, 5.96; N, 9.41; Gd, 21.14; found: C, 35.41; H, 6.04; N, 9.16; Gd, 20.98;

Example 3

Synthesis of Dicyclohexylenetriaminepentaacetic acid Isomer (DCTPA') (8)

A. t-Butyl DCTPA' (7): A mixture of the dicyclohexylenetriamine 3B (7.8 g, 37 mmol), t-butyl bromoacetate (40 ml, 246 mmol), potassium carbonate (25.5 g), molecular sieves (4Å 20 g) in anhydrous acetonitrile was stirred at 50° C. for 2 days. The same procedure used in the synthesis of t-butyl DCTPA 4 in Example 1, Part D above provided 7 as a white solid (22 g, 76%); mp 107°–109° C. $^1$H NMR (360 MHz, CDCl$_3$) δ: 3.64–3.51 (m, 10H, CH$_2$), 2.75 (m, 2H), 2.57 (m, 2H), 2. 1.47, 1.45 (2s, 49H, CH 3), 1.23–1.08 (m, 8H): $^{13}$C NMR (300MHz, CDCl$_3$) 67 : 172.86, 170.28, 66.23, 63.23, 47.96, 29.04, 27.10, 27.03, 25.05, 24.89. HRMS (PK match, LSIMS, CH$_2$Cl$_2$-MeOH) calc'd for $C_{42}H_{72}N_2O_{10}$ $(M+H)^+$782.545307, found $(M+H)^+$ 782.54987.

B. DCTPA' (8): Following the same procedure used in synthesis of DCTPA (5) in Example 1, Part E above, DCTPA' 8 was synthesized in 80% yield. mp 178° C.; 1H NMR (360 MHz, DMSO-d$_6$) δ:3.76 (d, 1H, J=65.1), 3.71 (d, 1H, J=65.8), 3.61 (d, 4H, J=44.5), 3.56 (d, 4H, J=44.5), 3.15 (m, 2H), 2.86 (m, 2H), 2.30 m, 2H), 2.09 (m, 2H), 1.61 (m, 4H), 1.30-1.08 m; $^{13}$C NMR (DMSO-d6)δ: 172.92, 170.17, 68.22, 63.203 46.97 28.27 26.77, 24.90, 24.66; HRMS (PK match, LSIMS, MeOH/DMSO) calc'd for $C_{22}H_{35}N_3O_{10}(M+H)^+$ 502.24007, found $(M+H)^+$ 502.23841; Elemental Analysis Calc'd for $C_{22}H_{35}N_5O_{10}$: C, 52.67, H, 7.03, N, 8.33; found C, 52.48; H, 7.01; N, 8.33.

Example 4

Gadolinium Complex of DCTPA' (9):

The gadolinium complex of DCTPA' (9) was prepared using the procedure of Example 2 above; mp 230° C. (dec.).

Example 5

Imaging studies with Gadolinium complex of DCTPA (6)

The gadolinium complex of DCTPA (6) from Example 2 was used in magnetic resonance imaging studies of rabbits. The gadolinium complex of DCTPA (6) was studied in three doses (10, 30 and 100 micromoles per kg), using heavily T1-weighted magnetic resonance sequences (TR 400, TE 12 mSec) at 1.5 T. The experiments were performed with one rabbit at each dose. Each rabbit was anesthetized during imaging and imaging periods were pre-administration of 6, 15 min., 30 min. 60 min. and 24 hours after administration of (6).

For liver imaging, at 10 μM/kg, the visual and quantitative enhancement was not clear. However, at 30 μM/kg, visual and quantitative enhancement of the liver was satisfactory. At 100 μM/kg, visual and quantitative enhancement of the liver was also satisfactory. Clearance of 6 from the liver is complete by 24 hours. Imaging of the kidney cortex and medulla showed a similar result, with the 10 μM/kg dose of 6 producing a less desirable result than the 30 μM/kg or 100 μM/kg doses.

What is claimed is:

1. A compound of the formula

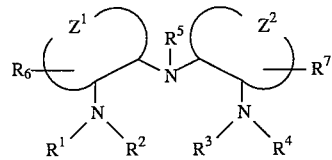

wherein $Z^1$ and $Z^2$ each represent the atoms necessary to complete a monocyclic or polycyclic carbocyclic or heterocyclic ring system, said $Z^1$ and $Z^2$ independently optionally substituted with $R^6$ and $R^7$, respectively;

$R^1$, $R^2$, $R^3$ and $R^4$ are independently carboxyalkyl ($C_1$–$C_2$), —$(CH_2)_n$—$C(=O)$—$NH$—$R^8$, or —$(CH_2)_n$—$C(=O)$—$O$—$R^8$, $R^5$ is carboxyalkyl ($C_1$—$C_2$);

$R^6$ and $R^7$ are independently hydrogen, benzyl, or benzyloxy, said benzyl or benzyloxy optionally substituted with one, two or three substituents selected from the group consisting of amino, isocyanato (—N=C=O), isothiocyanato (—N=C=S), —NH—C(=O)—X or —NH—C(=S)—X;

$R^8$ is alkyl ($C_1$–$C_{20}$), —$(CH_2)_m$—Ar, or polyhydroxyalkyl ($C_1$–$C_{20}$);

n is 1 or 2;

m is 1 to 15;

X is a targeting moiety; and

Ar is phenyl optionally substituted with one, two or three substituents selected from the group consisting of amino, acylamino, hydroxy, alkyl (C1–C5) and halogen.

2. A compound of claim 1 wherein $Z^1$ and $Z^2$ each represent the atoms necessary to complete a mono-, bi- or tricyclic carbocyclic or heterocyclic ring system.

3. A compound of claim 2 wherein $Z^1$ and $Z^2$ each represent the atoms necessary to complete a monocyclic carbocyclic or heterocyclic ring system.

4. A compound of claim 3 wherein $Z^1$ and $Z^2$ represent the atoms necessary to complete different monocyclic carbocyclic or heterocyclic ring systems.

5. A compound of claim 3 wherein $Z^1$ and $Z^2$ each represent the atoms necessary to complete the same monocyclic carbocyclic or heterocyclic ring system.

6. A compound of claim 5 wherein $Z^1$ and $Z^2$ each represent the atoms necessary to complete a cyclohexane ring.

7. A compound of claim 6 wherein $R^1$, $R^2$, $R^3$, $R^4$ and $R^5$ are each carboxymethyl.

8. A compound of claim 1 wherein $R^1$, $R^2$, $R^3$ and $R^4$ are independently carboxyalkyl ($C_1$–$C_2$).

9. A compound of claim 8 wherein $R^1$, $R^2$, $R^3$, and $R^4$ are each carboxymethyl.

10. A compound of claim 1 wherein $R^5$ is carboxymethyl.

11. A compound of claim 1 wherein $R^6$ and $R^7$ are independently hydrogen, substituted benzyl or substituted benzyloxy.

12. A compound of claim 1 further comprising a metal ion chelated with said compound.

13. A compound of claim 12 wherein said metal is a paramagnetic metal.

14. A compound of claim 13 wherein said paramagnetic metal is selected from the group consisting of Cr, V, Mn, Fe, Co, Ni, Cu, La, Ce, Pr, Nd, Pm, Sm, Eu, Gd, Tb, Dy, Ho, Er, Tm, Yb, and Lu.

15. A compound of claim 14 wherein said paramagnetic metal is Gd.

16. A pharmaceutical composition comprising a compound of claim 1 and a pharmaceutically acceptable carrier or diluent.

17. A pharmaceutical composition comprising a compound of claim 12 and a pharmaceutically acceptable carrier or diluent.

18. A method of providing an image of an internal region of a patient comprising administering to the patient a compound of the formula

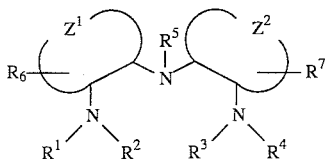

Formula I chelated with a paramagnetic metal ion wherein

Z1 and Z2 each represent the atoms necessary to complete a monocyclic or polycyclic carbocyclic or heterocyclic ring system, said Z1 and Z2 independently optionally substituted with $R^6$ and $R^7$, respectively;

$R^1$, $R^2$, $R^3$ and $R^4$ are independently carboxyalkyl ($C_1$–$C_2$), —$(CH_2)_n$—C(=O)—NH—$R^8$, or —$(CH_2)_n$—C(=O)—O—$R^8$ $R^5$ is carboxyalkyl ($C_1$–$C_2$);

$R^6$ and $R^7$ are independently hydrogen, benzyl, or benzyloxy, said benzyl or benzyloxy optionally substituted with one, two or three substituents selected from the group consisting of amino, isocyanato (—N=C=O), isothiocyanato (—N=C=S), —NH—C(=O)—X or —NH—C(=S)—X;

$R^8$ is alkyl ($C_1$–$C_{20}$), —$(CH_2)_m$—Ar, or polyhydroxyalkyl ($C_1$–$C_{20}$);

n is 1 or 2;

m is 1 to 15;

X is a targeting moiety; and

Ar is phenyl optionally substituted with one, two or three substituents selected from the group consisting of amino, acylamino, hydroxy, alkyl (C1–C5) and halogen; and; scanning the patient using magnetic resonance imaging to obtain visible images of the region.

19. The method of claim 18 wherein said compound is chelated with Gd.

20. The method of claim 18 wherein $Z^1$ and $Z^2$ each represent the atoms necessary to complete the same monocyclic carbocyclic or heterocyclic ring system.

21. The method of claim 20 wherein $Z^1$ and $Z^2$ each represent the atoms necessary to complete a cyclohexane ring.

22. The method of claim 21 wherein $R^1$, $R^2$, $R^3$, $R^4$ and $R^5$ are each carboxymethyl.

23. The method of claim 18 wherein $R^1$, $R^2$, $R^3$ and $R^4$ are independently carboxyalkyl ($C_1$–$C_2$).

* * * * *